(12) United States Patent
Milbocker et al.

(10) Patent No.: US 9,295,634 B2
(45) Date of Patent: Mar. 29, 2016

(54) TOPICAL WITH STATIC PHOTOBIOLOGICAL FUNCTIONALITY

(71) Applicant: Maple Ridge Group, LLC, New York, NY (US)

(72) Inventors: Michael Milbocker, Holliston, MA (US); Kenneth Rothaus, New York, NY (US)

(73) Assignee: Maple Ridge Group, LLC, New York, NY (US)

( * ) Notice: Subject to any disclaimer, the term of this patent is extended or adjusted under 35 U.S.C. 154(b) by 5 days.

(21) Appl. No.: 13/797,993

(22) Filed: Mar. 12, 2013

(65) Prior Publication Data

US 2014/0271503 A1    Sep. 18, 2014

(51) Int. Cl.
*A61K 8/90* (2006.01)
*A61Q 17/04* (2006.01)

(52) U.S. Cl.
CPC . *A61K 8/90* (2013.01); *A61Q 17/04* (2013.01); *A61K 2800/94* (2013.01)

(58) Field of Classification Search
CPC ...... A61K 2800/94; A61K 8/90; A61Q 17/04
See application file for complete search history.

(56) References Cited

U.S. PATENT DOCUMENTS

| | | | | |
|---|---|---|---|---|
| 4,373,057 | A * | 2/1983 | Hammond | 524/700 |
| 6,284,258 | B1 * | 9/2001 | Rose | A61K 8/46 424/401 |
| 7,988,953 | B2 * | 8/2011 | Poschalko | A61K 8/445 424/59 |
| 2002/0028875 | A1 * | 3/2002 | Anderle et al. | 524/591 |
| 2010/0189661 | A1 * | 7/2010 | Musa et al. | 424/40 |

* cited by examiner

*Primary Examiner* — Ernst V Arnold
(74) *Attorney, Agent, or Firm* — W. David Wallace; Holland & Knight LLP

(57) ABSTRACT

Compositions and methods thereof, for preventing or minimizing skin penetration and that promote surface-layer fixation of dermatological molecules in a human body are disclosed. The molecules of the present invention and compositions containing said molecules comprise a tissue-reactive part, an amphiphilic part, a light-functional part and optionally a detachment mechanism for releasing said tissue-reactive part from said light-functional part. The methods include ways of combining the tissue-reactive part, amphiphilic part, light-functional part and optionally synthesizing a detachment mechanism therein. The parts when combined form molecular structures possessing novel photobiological persistence and efficacy.

15 Claims, No Drawings

TOPICAL WITH STATIC PHOTOBIOLOGICAL FUNCTIONALITY

This application claims the benefit of the priority of U.S. provisional application 61/610,014, which is hereby incorporated by reference in its entirety.

BACKGROUND

Over exposure to sunlight can result in uncomfortable sunburn, premature aging of the skin, skin, wrinkles, loss of skin elasticity, dermatosis, and skin cancer. The most dangerous solar radiation is the ultraviolet (UV) radiation at wave lengths lower than 400 nm which includes both UV-A and UV-B radiation.

Sunscreen agents that primarily filter or absorb UV-A light are often referred to as UV-A absorbers. Similarly, sunscreen agents that primarily filter or absorb UV-B light are often referred to as UV-B absorbers. In general, the UV-A light refers to ultraviolet light having a wave length of 320-400 nm and UV-B light refers to ultraviolet light have a wave length of 280-320 nm.

A good UV absorbing chromophore should have excellent photostability, toxicological and dermatological acceptability, excellent heat stability, very good solubility in cosmetic solvents, compatibility with cosmetic bases, pH stability in the range of 4 to 9, processability into cosmetic formulations, compatibility with other ingredients of cosmetic formulations and with the packaging materials, no staining of textiles, no unpleasant odor, and it should be free of tackiness and have a low volatility.

Ultraviolet radiation can degrade photoactive substances by breaking down chemical bonds in the structure of a component such as a polymer. The absorbed radiation can excite the absorbing molecules and raise them to a higher energy level, which can be very reactive. If the molecule cannot be relaxed, bond cleavage and the formation of free radicals occurs. These free radicals can attack other molecules or components of tissue.

Accordingly, the performance of a photoactive compound or a combination of photoactive compounds in a sunscreen composition depends on these degradation processes, and the performance can degrade relatively quickly, for example, as is the case with avobenzone. Characterization of the rate of performance degradation requires expensive laboratory testing to determine the rate of loss of UV absorbance and a function of flux and duration. Moreover, a particularly difficult problem is presented when one photoactive compound in a sunscreen composition acts to increase the rate of photodegradation of another photoactive compound in the composition. Thus there is a need to immobilize in a segregated configuration different photoactive substances. The goal is to prevent a bimolecular reaction between two photoactive compounds when they come in contact, which lowers the threshold energy need to raise a photoactive compound to its excited state. For example, when avobenzone is combined with octyl methoxycinnamate a bimolecular pathway leads to the rapid photodegradation of both the dibenzoylmethane derivative and the octyl methoxycinnamate.

Most UV absorbing chromophores used in sunscreen compositions are monomeric compounds, and thus there is the inherent risk that such compounds penetrate the skin barrier, which is highly undesirable.

The present invention relates generally to compositions comprising chemical groups possessing a light absorbing or blocking function bonded to chemical groups possessing a tissue bonding function and methods of making and applying such compositions to mammalian skin. In particular, the present invention is directed towards compositions useful in the cosmetic or sunscreen industry in which one aspect prevents tissue infiltration, another aspect promotes permanence, and yet another aspect is photobiologically active. More particularly, the present invention details structures which are localized to the surface of tissue and minimize the depth to which potentially sensitizing components penetrate tissue, and other structures which bond to particular cellular types characteristic of a tissue surface, and other therapeutic structures which are optionally detachably connected to said bonding and infiltration preventing structures, in combination or separately, wherein said therapeutic structures are released from the skin surface over a selectable period of time.

Therefore, there is a demand for sunscreens which meet the above requirements and which, in particular, have a reduced risk of penetrating the skin and the components of which are immobilized against contact. The sunscreens should have comparably, preferably better properties than the sunscreens of the prior art, in particular they should combine a high SPF with a low risk of skin penetration, and a means for maintaining a desired SPF factor for a duration longer than the average expected exposure interval.

For example, a particularly advantageous family of UV-A screens is constituted by dibenzoylmethane derivatives, in particular 4-tert-butyl-4'-methoxydibenzoyl methane, which have intrinsically good absorbing powers. Unfortunately, it has been discovered that dibenzoylmethane derivatives are relatively sensitive to ultraviolet radiation (in particular UV-A), i.e., more precisely, they have an annoying tendency to degrade at a greater or lesser rate under the action thereof. This substantial lack of photochemical stability of dibenzoylmethane derivatives to the ultraviolet radiation to which they are by their very nature intended to be subjected cannot guarantee constant protection during prolonged exposure to the sun, and repeated applications at regular, close intervals have to be made by the consumer to effectively protect the skin against UV radiation.

Heretofore, a number of patents have disclosed sun block compositions, compositions containing biologically active molecules and combinations. The relevant portions of which may be briefly summarized as follows:

U.S. Pat. No. 8,128,913 describes a sunscreen composition comprising a skin bonding polymer composition comprising a hydrophobic polymer/hydrophilic polymer adduct, at least one sunscreen active agent comprising a UV-A absorber, and water in an amount of affected to provide a the composition with the texture suitable for application to skin.

U.S. Pat. No. 8,025,867 describes a photostable, topically applicable cosmetic/dermatological compositions contain at least one dibenzoylmethane compound UV-A sunscreen and at least one merocyanine sulfone compound.

U.S. Pat. No. 7,988,953 describes a conjugate comprising a hyperbranched polymer covalently bonded to at least three UV absorbing chromophores having an UV absorption U.S. Pat. No. 7,981,402 describes polymers containing one or more novel photoactive moieties, sunscreen compositions including a mixture of a photoactive compound and a polymer containing one or more photoactive moieties.

U.S. Pat. No. 7,910,090 describes a base composition that allows for the formulation of non-irritating cosmetic and/or dermatological compositions.

U.S. Pat. No. 7,897,779 describes novel 1,4-dihydropyridine derivatives and novel cosmetic or dermatological sunscreen compositions containing these derivatives.

U.S. Pat. No. 7,892,524 describes an organic sunscreen agent dispersed within a condensation polymerized resin having carboxylic acid groups.

U.S. Pat. No. 7,799,317 describes polymers containing one or more novel photoactive moieties, sunscreen compositions including a mixture of a photoactive compound and a polymer containing one or more photoactive moieties.

U.S. Pat. No. 7,790,202 describes a multi-purpose skin composition which functions as a sunscreen, an anti-perspirant, an insect/pest repellant and/or an antiseptic.

U.S. Pat. No. 7,674,764 describes a composition for controlled release of an active material such as a fragrance, sunscreen, vitamin or biocide in a product.

U.S. Pat. No. 7,534,421 describes a stable, topically applicable cosmetic/dermatological sunscreen compositions, well suited for the UV-photoprotection of human skin/keratinous materials, containing a thus effective amount of at least one novel s-triazine compound bearing at least one para-aminobenzalmalonic salt substituent.

U.S. Pat. No. 7,416,721 describes a sunscreen compositions having improved comfort after application U.S. Pat. No. 7,384,916 describes methods for treating aging and photodamaged skin employing topical application of compositions which comprise at least one peptide manganese complex.

U.S. Pat. No. 7,374,749 describes amino substituted hydroxyphenyl benzophenone derivatives.

U.S. Pat. No. 7,326,408 describes topical sunscreens obtained by combining a topical sunscreen agent in a formulation containing an antibacterial medication such as azelaic acid or an antibiotic.

U.S. Pat. No. 7,326,407 describes a stable, topically applicable cosmetic/dermatological sunscreen compositions, well suited for the UV-photoprotection of human skin/keratinous materials, containing an effective amount of at least one novel amine, amide, sulphonamide or carbamate substituted benzalmalonic salt compound.

U.S. Pat. No. 7,235,587 describes diesters containing two crylene or fluorene moieties, sunscreen compositions containing the same, and methods of photostabilizing a sunscreen composition.

U.S. Pat. No. 7,153,494 describes a topically applicable photostable sunscreen/photoprotective compositions contain at least one dibenzoylmethane UV-sunscreen and an effective photostabilizing amount therefor of at least one amphiphilic block copolymer which comprises at least one nonionic hydrophilic polymer block and at least one hydrophobic polymer block, formulated into a topically applicable, cosmetically acceptable medium.

U.S. Pat. No. 6,284,258 describes compounds that are two-part molecules, and compositions containing such compounds, in which one part is designed to become covalently bonded to the skin (bonding agent) and the other part (a characteristic use agent) is designed to impart some characteristic use, such as emolliency, moisturizing effect, anti-acne, anti-wrinkle, anti-pain, antimicrobial, antifungal, antiviral, anti-irritation, skin tanning and skin lightening effects, extended protection of the skin (e.g., from ultraviolet light, by incorporation of a sunscreen component.

U.S. Pat. No. 5,951,967 describes a multi-phase sunscreen agent, characterized by at least two phases that are liquid to pasty or gelatinous and separate from each other spontaneously within seconds to less than ten minutes after a brief and gentle mixing process lasting less than one minute without any essential application of force, where at least one phase contains a UV filter.

U.S. Pat. No. 4,844,884 describes cosmetic sunscreen products which contain a tyrosine derivative.

A typical topical sunscreen has no mechanism for chemically fixating to the exterior tissue layers comprising skin. Compositions relying on hydrophobicity are commonly mechanically wiped away by towels and the like. Compositions that diffuse into skin typically do not penetrate deeply and rely on a concentration gradient where the location of maximum concentration is at the skin surface. As the concentration at the skin surface is depleted by mechanical dissociation, the concentration gradient reverses direction, wherein the higher concentration within tissue causes the infiltrated composition to begin diffusing to the skin surface. Accordingly, such compositions do not reside long within the skin in physiologically significant concentration, typically less than a few hours. And the allowance of skin penetration to the level of living tissue can result in sensitization, allergic reaction, and immunological response.

There is a need for augmenting tissue residence time of dermatological preparations. Therefore it is an object of the present invention to provide molecular species for delivering dermatologically active molecules to tissue comprising one or more of the following: a) the formation of a bond between said dermatological molecule and a specific layer of skin, b) the localization of said dermatological molecules to a specific layer of skin, and c) the sequestration of multiple photoactive components on a single molecule in a manner that prevents them from interacting in a degradational mode.

It is further an object of the present invention to provide methods and compositions for modifying a tissue surface. For example, bonding protective molecules so as to protect the underlying tissue layers from solar radiation, allergens, microbes, chemical toxins and the like. It is further an object of the present invention to provide methods and compositions for conditioning a surface. For example, one or more of the steps of improving the resiliency or feel of a tissue layer, reducing the surface tension between topical preparation and tissue structures, modifying the electrical charge or energy state of a tissue structure, modifying the nucleophilicity of a tissue structure including modifying its hydrophobicity and oleophobicity. It is further an object of the present invention to provide methods and compositions for facilitating release of a biologically active substance at a specific tissue layer. For example, adding one or more functional groups which bond to a tissue layer in a biologically inactive state and are subsequently released by local metabolic and chemical processes, or adding one or more enhancers which bond to a tissue surface and are required for activation or release of a biologically active substance.

It is further an object of the present invention to provide methods and compositions for increasing the functionality of an enhancer molecule to enable a multiplicity of biologically active processes. For example, adding one or more tissue-reactive functional groups, increasing the number and density of a tissue-reactive functional group, reducing the mean molecular weight of a carrier molecule while maintaining or increasing the number of functional groups per mean molecular weight, and adding an optional tractor functionality to a dermatological composition which creates a reverse gradient and biological functionality which bonds to an adverse molecule and transports said bonded pair to the skin surface.

There is a need for dermatological preparations comprising sunscreens with a palliative component which provides a rapid initial bolus of biologically active molecules, wherein the reactions responsible for this first curative state do not fully fixate the composition and leave it transportable and in a tissue-reactive state, and subsequently this tissue-reactive state and tissue bonding functionality persists for some time to enable deep penetration.

Finally, it is an object of the present invention to provide tissue bonding systems comprised of two distinct phases wherein the second phase releases photobiologically active components from the tissue at a desired time.

It is further an object of the present invention that the first tissue bonding phase reaches a high fixation state quickly while leaving most of its biologically active functionality unchanged and remains in that state for an extended period of time.

It is another object of the present invention that the second biologically active phase modifies tissue and provides biological functionality for an extended period of time.

SUMMARY

A sunscreen composition that provides stability to a UV-A absorber is described. The sunscreen composition includes a skin bonding polymer composition comprising an amphiphilic polymer adduct, and at least one sunscreen active agent comprising a UV-A absorber. These compositions are typically anhydrous.

Tissue bonding dermatological compositions and methods of synthesis are provided for modifying tissue, and specifically skin, by enabling an enhanced reduction in UV radiation and in combination or separately a chemical bond between the photobiologically active species and tissue. The dermatological composition polymerizes to a specific tissue layer and then transitions to a release state, wherein the photobiologically active group is released after a desired period of time.

The basic tissue bonding structure is a trifunctional pluronic wherein three diisocyanates are attached, and alternatively biologically active species are attached to one or more of the pendant NCO groups. The diisocyanate can be any aromatic or allophatic diisocyanate, and preferably one with minimal skin sensitization properties. For example, 1,1'methylene-bis-[4,isocyanatocyclohexane]. Structures of this kind will be referred to in the remainder of this disclosure as a tissue-functional molecule or component.

Biologically active species, other than sun screen components, suitable in the present invention is selected from the group consisting of agents that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratolytic agents; antiperspirants; antipsoriatic agents; antiseborrheic agents; hair conditioners and hair treatment agents; antiaging and antiwrinlde agents; sunblock and sunscreen agents; skin lightening agents; depigmenting agents; vitamins; corticosteroids; tanning agents; hormones; amino acids; dipeptides; tripeptides; oligopeptides; polypeptides; retinoids; topical cardiovascular agents; hydroxyacids, ketoacids and related compounds; phenyl alpha acyloxyalkanoic acids and derivatives thereof; and N-acetyl-aldosamines, N-acetylamino acids and related N-acetyl compounds.

The tissue-functional molecule may be bonded to or mixed in solution with various molecules intended to restore moisture or resilience to skin. These are commonly referred to as cosmetic base compositions. Compositions exhibiting therapeutic properties include sucrose fatty acid esters and fatty acid lactylates, with or without shea butter. Such topical compositions are known to demonstrate enhanced wound healing properties and decreased sensitivity to UV light.

Other cosmetic base compositions of the present cosmeceutical is selected from the group consisting of aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), .gamma.-aminobutanoic acid, aminocaproic acid, aminosalicylic acid, amitriptyline, anserine, anthralin, ascorbic acid, ascorbyl palimate, atropine, azelaic acid, bacitracin, bemegride, beclomethasone dipropionate, benzocaine, benzophenone, benzoyl peroxide, betamethasone dipropionate, betamethasone valerate, brompheniramine, bupivacaine, butoconazole, calcipotriene, camphor, capsaicin, carbamide peroxide, carnosine, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexamethasone, diphenhydramine, doxypin, doxylamine, dyclonine, econazole, erythroinycin, estradiol, ethinyl estradiol, fluocinocide, fluocinolone acetonide, 5-fluorouracil, glutathione, griseofulvin, guaifenesin, haloprogin, hexylresorcinol, homocarnosine, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, imiquimod, indomethacin, ketoconazole, ketoprofen, kojic acid, lidocaine, meclizine, meclocycline, menthol, mepivacaine, methyl nicotinate, methyl salicylate, metronidazole, miconazole, minocycline, minoxidil, monobenzone, mupirocin, naftifine, naproxen, neomycin, nystatin, octyl methoxycinnamate, octyl salicylate, ophidine, ornithine, oxybenzone, oxiconazole, oxymetazoline, padimate O, permethrin, pheniramine, phenol, phenylephrine, phenylpropanolamine, piperonyl butoxide, podophyllin, podofilox, povidone iodine, polymyxins, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmiltate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, zinc pyrithione, glycolic acid, lactic acid, methyllactic acid, 4-hydroxy-mandelic acid, mandelic acid, gluconolactone, N-acetyl-glucosamine, N-acetyl-proline, phenyl 2-acetoxyethanoic acid and diphenyl 2-acetoxyethanoic acid.

The tissue-functional molecule of the present invention is capable of forming a gel matrix on the surface or at various layers within the skin. This gel forming aspect of the present invention can be enhanced by the addition of at least one compound selected from the group consisting of lactobionic acid, isolactobionic acid, maltobionic acid, isomaltobionic acid, cellobionic acid, gentiobionic acid, laminarabionic acid, melibionic acid, nigerobionic acid, rutinobionic acid, sophorobionic acid, and kojibionic acid as isomeric, nonisomeric, free acid, ester, salt, partial salt, lactone, saturated or unsaturated, straight or branched chain, or cyclic form thereof.

The tissue-functional molecule of the present invention can be modified to reach deeper layers of the skin by attaching one or more tissue penetrating species to one or more pendant NCO groups. Sorbitan esters of long chain aliphatic acids are suitable in the present invention as permeation enhancers.

Skin permeation enhancement using aliphatic alcohol esters of lactic acid, myristyl Lactate and lauryl lactate, acyl lactylates, caproyl lactylic acid and lauroyl lactylic acid are also contemplated.

Alternatively, a tissue-functional molecule can be formed by adding NCO groups to an alkenyl group which may be either straight or branched chained and whose hydroxy substituents are endcapped with diisocyanate.

The permeation modulator may be attached directly to the tissue-functional molecule or mixed in solution. The permeation modulator may be an alkanoic or alkenic acid, preferably having 6 to 20 carbon atoms such as capric acid, octanoic acid, oleic acid or acids or such acids of intermediate chain length. The permeation modulator aids the penetration of the tissue-functional molecule through the stratum corneum, the principle barrier to the penetration of drugs. The stratum corneum is an aggregate of the stacked, flattened skeletons of keratin filled cells interspersed with lipid monolayer structures and water. The addition of the permeation modulator to the formulation results in the partial disruption of the barrier components, particularly the lipid structures. A gradient of the tissue-functional molecule can be produced across the stratum corneum particularly, which facilitates the diffusion of a detachable biologically active group attached to the tissue-functional molecule, such as nitric oxide, across the stratum corneum into the living epidermis.

In still other compositions of the present invention, it may be desirable to reduce the oiliness of a composition or its feel on skin. Representative compounds that can be used include the following: (2-hydroxy-3-octadecylthio propyl)dimethylamine hydrochloride, 4-(3-decylthio-2-hydroxy propyl) morpholinium tartrate, (3-hexadecylthio-2-hydroxy propyl) bis(.beta.-hydroxyethyl)amine hydrochloride, [3-(2,2-dimethoxy ethylthio)-2-hydroxy propyl]dimethylamine hydrochloride, [2-hydroxy-3-(2-pyridyl thio)propyl]dimethylamine dihydrochloride, [2-hydroxy-3-(2-pyridyl ethylthio)propyl]diethylamine dihydrochloride, (3-benzylthio-2-hydroxy propyl)diisopropylamine hydrochloride, (3-benzylthio-2-hydroxy propyl)diethylamine hydrochloride, (3-p-chlorobenzylthio-2-hydroxy propyl)diethylamine hydrochloride, [3-(p-butoxybenzylthio)-2-hydroxy propyl] bis(2-hydroxy ethyl)amine, [2-hydroxy-3-(o-methylbenzylthio)propyl]diethylamine, (2-hydroxy-3-phenylthio propyl)dicyclohexylamine, (3-o-amino-phenylthio-2-hydroxy propyl)diethylamine, 3-(2-hydroxy-3-morpholino propylthio)alanine, [2-hydroxy-3-(2-chlorobenzamido ethylthio)propyl]diethylamine,

DETAILED DESCRIPTION

The present sunscreen composition includes a sunscreen agent bonded to a skin bonding polymer composition, and anhydrous base. The sunscreen composition can include additional components commonly found in sunscreens composition including, for example, surfactants, pH adjusting agents, thickeners, emollients, moisturizers, coloring agents, preservatives, antioxidants, chelating agents, and fragrances.

The sunscreen agent includes a UV-A absorber. In general, certain UV-A absorbers, such as oxybenzophenone and avobenzone have a tendency to lose effectiveness as a UV-A absorber as a result of exposure to light. Octocrylene is a UV-B absorber that provides some UV-A absorptions (is sometimes characterized as a UV-A absorber) but tends to lose effectiveness as a UV-A absorber as a result of expose to light. The skin bonding polymer composition that is provided as part of the sunscreen composition can be constructed to enhance the stability of the UV-A absorber so that the sunscreen composition provides protection against UV-A for a longer period of time compared with sunscreen compositions that do not enhance the stability of the UV-A absorber.

In general, a UV-A absorber refers to a component having a primary or maximum UV absorption in the UV-A range of 320-400 nm. A UV-B absorber refers to a component having a primary or maximum UV absorption in the UV-B range of 280-320 nm. The maximum or primary UV absorbance refers to the wave length at which a maximum amount of light is absorbed. The characterization can be evaluated by running a UV spectrum.

Exemplary dibenzoylmethane compounds according to the invention include: 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane.

The compositions in accordance with the invention will preferably comprise other complementary organic or inorganic photoprotective agents which are active in the UV-A and/or UV-B region, which are hydrophilic or lipophilic or even insoluble in the cosmetic solvents in routine use.

The complementary organic photoprotective agents are selected in particular from anthranilates; cinnamic derivatives; salicylic derivatives; camphor derivatives; benzophenone derivatives; diphenylacrylate derivatives; triazine derivatives; benzotriazole derivatives; benzalmalonate derivatives, in particular benzimidazole derivatives; imidazolines; bis-benzoazolyl derivatives; p-aminobenzoic acid (PABA) derivatives; methylene bis-(hydroxyphenyl benzotriazole) derivatives; benzoxazole derivatives; polymeric screens and silicone screens; dimeric .alpha.-alkylstyrene derivatives; 4,4-diarylbutadienes and mixtures thereof. Examples of complementary organic photoprotective agents which are representative are those designated below under their INCI names:

Para-aminobenzoic Acid Derivatives: PABA; Ethyl PABA; Ethyl Dihydroxypropyl PABA; Ethylhexyl Dimethyl PABA, marketed in particular under the trademark “ESCALOL 507” by ISP; Glyceryl PABA; PEG-25 PABA, marketed under the trademark “UVINUL P25” by BASF;

Salicylic Derivatives Homosalate, marketed under the trademark “Eusolex HMS” by Rona/EM Industries; Ethylhexyl Salicylate, marketed under the trademark “NEO HELIOPAN OS” by HAARMANN and REIMER; Dipropyleneglycol Salicylate, marketed under the trademark “DIPSAL” by SCHER; TEA Salicylate, marketed under the trademark “NEO HELIOPAN TS” by HMRMANN and REIMER;

Cinnamic Derivatives: Ethylhexyl Methoxycinnamate, marketed in particular under the trademark “PARSOL MCX” by HOFFMANN LA ROCHE; Isopropyl Methoxy cinnamate; Isoamyl Methoxy cinnamate, marketed under the trademark “NEO HELIOPAN E 1000” by HMRMANN and REIMER; Cinoxate; DEA Methoxycinnamate; Diisopropyl Methylcinnamate; Glyceryl Ethylhexanoate dimethoxycinnamate;

Diphenylacrylate Derivatives: Octocrylene, marketed in particular under the trademark “UVINUL N539” by BASF; Etocrylene, marketed in particular under the trademark “UVINUL N35” by BASF;

Benzophenone Derivatives: Benzophenone-1, marketed under the trademark “UVINUL 400” by BASF; Benzophenone-2, marketed under the trademark "UVINUL D50" by BASF; Benzophenone-3 or Oxybenzone, marketed under the trademark "UVINUL M40" by BASF; Benzophenone-4, marketed under the trademark "UVINUL MS40" by BASF; Benzophenone-5; Benzophenone-6, marketed under the trademark "Helisorb 11" by Norquay; Benzophenone-8, marketed under the trademark "Spectra-Sorb UV-24" by American Cyanamid; Benzophenone-9, marketed under the trademark "UVINUL DS-49" by BASF; Benzophenone-12; n-Hexyl 2-(4-diethylamino-2-hydroxybenzoyl)benzoate, marketed under the trademark "UVINUL A+" by BASF;

Benzylidene Camphor Derivatives: 3-benzylidene camphor made under the trademark "MEXORYL SD" by CHIMEX; 4-methyl benzylidene camphor, marketed under the trademark "EUSOLEX 6300" by MERCK; Benzylidene Camphor Sulfonic Acid, made under the trademark "MEXORYL SL" by CHIMEX; Camphor Benzalkonium Methosulfate, made under the trademark "MEXORYL SO" by CHIMEX; Terephthalylidene Dicamphor Sulfonic Acid, made under the trademark "MEXORYL SX" by CHIMEX; Polyacrylamidomethyl Benzylidene Camphor, made under the trademark "MEXORYL SW" by CHIMEX;

Phenyl Benzimidazole Derivatives: Phenylbenzimidazole Sulfonic Acid, marketed under the trademark "EUSOLEX 232" by MERCK; Disodium Phenyl Dibenzimidazole Tetrasulfonate, marketed under the trademark "NEO HELIOPAN AP" by HMRMANN and REIMER;

Phenyl Benzotriazole Derivatives: Drometrizole Trisiloxane, marketed under the trademark "Silatrizole" by RHODIA CHIMIE; Methylene bis-Benzotriazolyl Tetramethylbutylphenol, marketed in the solid form under the trademark "MIXXIM BB/100" by FAIRMOUNT CHEMICAL or in the micronized form in aqueous dispersion under the trademark "TINOSORB M" by CIBA SPECIALTY CHEMICALS;

Triazine Derivatives: Bis-Ethylhexyloxyphenol Methoxyphenyl Triazine, marketed under the trademark "TINOSORBS" by CIBA GEIGY; Ethylhexyl triazone, marketed under the trademark "UVINUL T150" by BASF; Diethylhexyl Butamido Triazone, marketed under the trademark "UVASORB HEB" by SIGMA 3V; 2,4,6-Tris(dineopentyl-4'-aminobenzalmalonate)-s-triazine; 2,4,6-Tris-(diisobutyl-4'-aminobenzalmalonate)-s-triazine.

Anthranilic Derivatives: Menthyl anthranilate, marketed under the trademark "NEO HELIOPAN MA" by HMRMANN and REIMER;

Imidazoline Derivatives: Ethylhexyl Dimethoxybenzylidene Dioxoimidazoline Propionate; Benzalmalonate Derivatives: Di-neopentyl 4'-methoxybenzalmalonate; Polyorganosiloxane with benzalmalonate functions, such as Polysilicone-15, marketed under the trademark "PARSOL SLX" by HOFFMANN LA ROCHE; 4,4-Diarylbutadiene derivatives: 1,1-Dicarboxy(2,2'-dimethylpropyl)-4,4-diphenylbutadiene;

Benzoxazole Derivatives: 2,4-Bis-[5-1 (dimethylpropyl) benzoxazol-2-yl-(4-phenyl)-imino]-6-(2-ethylhexyl)-imino-1,3,5-triazine, marketed under the trademark "Uvasorb K2A" by Sigma 3V; and mixtures thereof.

Inorganic photoprotective agents are selected from pigments or nanopigments (mean primary particle size: generally from 5 nm to 100 nm, preferably from 10 nm to 50 nm) of metallic oxides which may or may not be coated, for example titanium oxide nanopigments (amorphous or crystalline in the rutile and/or anatase form), iron, zinc, zirconium or cerium, and mixtures thereof. Conventional coating agents include alumina and/or aluminum stearate. Such metallic oxide nanopigments, which may or may not be coated.

The additional photoprotective agents are generally present in the compositions according to the invention in proportions of 0.01% to 20% by weight with respect to the total composition weight, preferably 0.1% to 10% by weight with respect to the total composition weight.

The compositions of the invention may be in any of the forms which are suitable for topical application, in particular in the form of aqueous gels, in the form of emulsions obtained by dispersion of a fat phase (also termed the oily phase) in an aqueous phase (O/W) or the reverse (W/H), or multiple emulsions (for example W/O/W or O/W/O or O/O/W). They may be more or less fluid and have the appearance of a white or colored cream, a pomade, a milk, a lotion, a serum, a paste, a powder, a solid stick, and may optionally be packaged as an aerosol and in the form of a foam or spray. These compositions are prepared using the usual methods.

In a particular embodiment of the invention, the composition is in the form of an emulsion and then comprises at least one oily phase. The proportion of the oily phase of the emulsion may be from 1% to 80% by weight, preferably 2% to 50% by weight and more preferably 2% to 40% by weight with respect to the total composition weight. The fats in the oily phase, in particular oils, and the emulsifying and co-emulsifying agents which may be present, used in the composition in the form of an emulsion are selected from those conventionally used in the cosmetics or dermatological field. The emulsifying and co-emulsifying agent, when present, are generally present in a proportion of 0.1% to 30% by weight, preferably 0.3% to 20% by weight and more preferably 0.5% to 15% by weight with respect to the total composition weight. The emulsion may also contain lipid vesicles in addition to or in place of the emulsifying and/or co-emulsifying agents.

The emulsions generally contain at least one emulsifying agent selected from amphoteric, anionic, cationic or nonionic emulsifying agents used alone or as a mixture. The emulsifying agents are suitably selected as a function of the continuous phase of the emulsion to be produced (W/H or O/w). When the emulsion is a multiple emulsion, it generally comprises an emulsifying agent in the primary emulsion and an emulsifying agent in the external phase into which the primary emulsion is introduced.

Emulsifying agents which may be used to prepare W/H emulsions which may be cited, are for example alkyl esters or sorbitan ethers, glycerol or sugars; silicone surfactants such as dimethicone copolyols, such as the mixture of cyclomethicone and dimethicone copolyol, marketed under the trademarks DC 5225 C and DC 3225 C by Dow Corning and such as alkyl-dimethicone copolyols such as Laurylmethicone copolyol marketed under the trademark "Dow Corning 5200 Formulation Aid" by Dow Corning, Cetyl dimethicone copolyol marketed under the trademark Abil EM 90® by Goldschmidt and the mixture of Polyglyceryl-4 isostearate/Cetyl dimethicone copolyol/Hexyl laurate marketed under the trademark Abil WE 09® by Goldschmidt. It is also possible to add thereto one or more co-emulsifying agents which, advantageously, may be selected from the group comprising esters of fatty acids with a branched chain and polyol, in particular esters of fatty acid with a branched chain and glycerol and/or sorbitan and, for example, polyglyceryl isostearate, such as the product marketed under the trademark Isolan GI 34 by Goldschmidt, sorbitan isostearate, such as the product marketed under the trademark Arlacel 987 by ICI, sorbitan isostearate and glycerol, such as the product marketed under the trademark Arlacel 986 by ICI, and mixtures thereof.

Examples of emulsifying agents suitable for the preparation of O/W emulsions which may be cited are nonionic emulsifying agents such as esters of fatty acids and oxyalkylenated polyols (more particularly polyoxyethylenated), for example polyethylene glycol stearates such as PEG-100 stearate, PEG-50 stearate and PEG-40 stearate; esters of fatty acids and oxyalkylenated sorbitan comprising 20 to 100 OE, for example, and for example those marketed under the trademark Tween 20 or Tween 60 by Uniqema; ethers of oxyalkylenated (oxyethylenated and/or oxypropylenated) fatty alcohols; esters of sugars, alkoxylated or not, such as sucrose stearate and such as PEG-20 methylglucose sesquistearate; sorbitan esters such as sorbitan palmitate marketed under the trademark Span 40 by Uniqema; esters of a dibasic acid and a fatty alcohol, such as dimyristyl tartrate; mixtures of these emulsifying agents such as a mixture of glyceryl stearate and PEG-100 stearate (CTFA name: Glyceryl Stearate/PEG-100 Stearate) marketed under the trademark Arlacel 165 by Uniqema and under the trademark SIMULSOL 165 by SEPPIC; or the mixture of dimyristyl tartrate, cetearyl alcohol, Pareth-7 and PEG-25 laureth-25, marketed under the trademark Cosmacol PSE by Sasol (CTFA name: Dimyristyl tartrate/cetearyl alcohol/12-15 Pareth 7/PPG 25 laureth 25); mixtures of fatty alcohols and alkylglycoside, such as the cetearyl alcohol/cetearyl glucoside mixture, for example the commercially available product marketed under the trademark MONTANOV 68 by SEPPIC.

Co-emulsifying agents may be added to said emulsifying agents, such as fatty alcohols containing 8 to 26 carbon atoms, such as cetyl alcohol, stearyl alcohol and a mixture thereof (cetearyl alcohol), octyldodecanol, 2-butyloctanol, 2-hexyldecanol, 2-undecylpentadecanol or oleic alcohol, or fatty acids, for example.

Examples of oils which can be used in the compositions of the invention are hydrocarbon-containing oils of animal origin such as perhydrosqualene (or squalane); hydrocarbon-containing oils of vegetable origin, such as caprylic/capric acid triglycerides such as those marketed by Stearineries Dubois or those marketed under the trademark Miglyol 810, 812 and 818 by Dynamit Nobel, or oils of vegetable origin, for example sunflower, corn, soya, gourd, grapeseed, sesame, hazelnut, apricot, macadamia nut, arara, coriander, castor, avocado, jojoba oil, shea butter oil; synthesized oils; silicone oils such as volatile or non-volatile polymethylsiloxanes (PDMS) with a linear or cyclic silicone chain, which are liquid or pasty at ambient temperature; fluorinated oils such as partially hydrocarbonated and/or silicone oils, such as those described in JP-A-2-295912; ethers such as dicapryl ether (CTFA name: Dicaprylyl ether); and benzoates of $C_{12}$-$C_{15}$ fatty alcohols (Finsolv TN from FINETEX); arylalkyl benzoate derivatives such as 2-phenylethyl benzoate (X-Tend 226 from ISP); amide oils such as isopropyl N-lauroylsarcosinate (ELDEW SL-205 from Ajimoto) and mixtures thereof.

The oily phase may also comprise one or more fats selected, for example, from fatty alcohols (cetyl alcohol, stearyl alcohol, cetearyl alcohol), fatty acids (stearic acid) and waxes (paraffin, polyethylene waxes, carnauba, beeswax).

The compositions of the invention may also contain one or more organic solvents which may be selected from the group constituted by hydrophilic organic solvents, lipophilic organic solvents, amphiphilic solvents or mixtures thereof.

Examples of hydrophilic organic solvents which are representative, for example, are linear or branched monohydric alcohols containing 1 to 8 carbon atoms, such as ethanol, propanol, butanol, isopropanol or isobutanol; polyethylene glycols containing 6 to 80 ethylene oxides; polyols such as propylene glycol, isoprene glycol, butylene glycol, glycerol or sorbitol; mono- or di-alkyl isosorbides the alkyl groups of which contain 1 to 5 carbon atoms, such as dimethyl isosorbide; glycol ethers such as diethylene glycol mono-methyl or mono-ethyl ether and propylene glycol ethers such as dipropylene glycol methyl ether.

Amphiphilic organic solvents which are exemplary include polypropylene glycol (PPG) derivatives, such as esters of polypropylene glycol and fatty acids, PPG and fatty alcohol such as PPG-23 oleyl ether and PPG-36 oleate.

Examples of lipophilic organic solvents which are exemplary are fatty esters such as diisopropyl adipate, dioctyl adipate or alkyl benzoates.

The compositions of the present invention may also comprise conventional cosmetic adjuvants selected from softeners, moisturizers, opacifying agents, stabilizers, emollients, silicones, anti-foaming agents, fragrances, preservatives, anionic, cationic, nonionic, zwitterionic or amphoteric surfactants, fillers, polymers, propellants, alkalinizing or acidifying agents or any other ingredient which is normally used in the cosmetics and/or dermatological field.

Hydrophilic thickeners which are exemplary include carboxyvinyl polymers such as carbopols (carbomers) and Pemulens (Copolymer acrylate/C10-C30-alkylacrylate); cellulose derivatives such as hydroxyethylcellulose; polysaccharides and in particular, gums such as xanthan gum; and mixtures thereof.

Lipophilic thickeners which are exemplary include modified clays, such as hectorite and its derivatives, for example products marketed under the trademark Bentone.

Preservatives which are exemplary include parahydroxybenzoic acid esters also known as Parabens® (in particular methyl paraben, ethyl paraben, propyl paraben), phenoxyethanol, formol liberators such as, for example, imidazolidinyl urea or diazolidinyl urea, chlorhexidine digluconate, sodium benzoate, caprylyl glycol, iodopropynyl butyl carbamate, pentylene glycol, alkyl trimethylammonium bromide such as myristyl-trimethylammonium bromide (CTFA name: Myrtrimonium bromide), dodecyl-trimethylammonium bromide, hexadecyl-trimethylammonium bromide, and mixtures thereof such as the mixture marketed under the trademark Cetrimide® by FEF CHEMICALS. The preservative may be present in the composition of the invention in an amount of 0.001% to 10% by weight with respect to the total composition weight, especially 0.1% to 5% by weight, and in particular 0.2% to 3% by weight.

Examples of fillers which may be included in the compositions of the invention are, for example, pigments; silica powder; talc; polyamide particles, in particular those marketed under the trademark ORGASOL by Atochem; polyethylene powders; powders of natural organic materials such as starch powders, in particular of corn, wheat or rice starch, which may or may not be cross-linked, such as powders of starch cross-linked by octenylsuccinate anhydride, marketed under the trademark DRY-FLO by National Starch; microspheres based on acrylic copolymers, such as those formed from an ethylene glycol dimethacrylate/lauryl methacrylate copolymer marketed by Dow Corning under the trademark POLYTRAP; polymethylmethacrylate powders such as those marketed under the trademark MICROPEARL M 100 by Matsumoto; expanded powders such as hollow microspheres, in particular microspheres marketed under the trademark EXPANCEL by Kemanord Plast or under the trademark MICROPEARL F 80 ED by Matsumoto; silicone resin microbeads, such as those marketed under the trademark TOSPEARL by Toshiba Silicone; polyurethane powders, such as hexamethylene diisocyanate/trimethylol hexyllactone copolymer marketed under the trademark Plastic Powder D-400 by Toshiba Pigment (CTFA name: HDI/Trimethylol Hexyllactone Crosspolymer); and mixtures thereof. When they are present, these fillers may be in quantities of 0.001% to 20% by weight, preferably 0.1% to 10% by weight and more preferably 1% to 5% by weight with respect to the total composition weight.

The compositions of the invention may constitute a skin care product, in particular for the face, the neck, the contours of the eye, the body; or a skin makeup product such as a tinting product (in particular a foundation), an eye shadow, a blusher, an eye-liner, a concealer, a body makeup product, a sun protection product or a skin cleansing product. Preferably, the composition of the invention is a sun protection product.

Skin Bonding Polymer Component

The sunscreen composition can include a skin bonding polymer component. The skin bonding polymer component can include any polymer that, when applied to the skin, helps hold the sunscreen agent to the skin. The skin bonding polymer component holds the sunscreen agent in proximity to skin tissue when applied to the skin tissue so that the sunscreen agent can protect the skin tissue from solar radiation. The skin bonding polymer component can be referred to as the polymer component. The polymer component can be provided as a polymer having an average molecular weight of at least about 2,000. The polymer component can be provided as a polymer having an average molecular weight of less than about 500,000.

The sunscreen composition can bind or adhere to skin tissue for a length of time, and can hold or contain the sunscreen agent within the composition. It is expected that the sunscreen composition is able to adhere or bind to skin tissue for at least about four hours and hold the sunscreen agent contained therein in proximity to skin tissue for at least that length of time.

Non-dendritic hyperbranched polymers are molecular constructions having a branched structure, generally around a core. In contrast to the highly symmetric structure of dendrimers, the structure of most non-dendritic hyperbranched polymers lacks symmetry: the base units or building blocks used in the construction of the non-dendritic hyperbranched polymer can be of different natures and they are distributed irregularly. The branches of the polymer can be of different natures and lengths. The number of building blocks can be different depending on the different branching.

Hyperbranched polymers may be synthesized e.g. by polycondensation or polyaddition of one or more building block, such as $AB_m$, wherein A and B are complementary functional groups capable of reacting with one another, m being an integer $\geq 2$, but other preparation processes can be envisaged.

For the purpose of the present specification a "building block" is preferably defined as a compound having at least three independent functional groups which may be involved in a polymerization reaction. Thus, a building block according to the present specification is a branched monomer. The term "building block" encompasses compounds having more than one kind of functional groups, such as $AB_m$ wherein $m \geq 2$, and compounds having only a single kind of functional group, such as $C_q$ wherein $q \geq 3$. Preferably, a building block has 50 atoms or less.

However, hyperbranched polymers may also be composed of more than one type of building block. For example, a hyperbranched polymer composed of n building blocks $AB_2$ and r building blocks $C_4$, wherein functional groups A are capable of reacting with functional groups C, but neither with functional groups A nor B. Furthermore, functional groups B are also capable of reacting with functional groups C, but neither with functional groups A nor B. Finally, functional groups C are not capable of reacting with one another. In consequence, the building blocks $AB_2$ may not react directly with one another; therefore, monomers $C_4$ are needed as "bridges" between functional groups A and A, A and B, and B and B. Such a hyperbranched polymer may be written as $(AB_2)_n(C_4)_r$. Since building block $AB_2$ as well as building block $C_4$ contains more than two functional groups, every addition of each building block results in an increase of the number of branches—every addition of building block $AB_2$ generates one further branch and every addition of building block $C_4$ generates 2 further branches.

Furthermore, hyperbranched polymers may also be composed of e.g. one type of building block in combination with a bifunctional monomer. For example, the above system comprising building blocks $AB_2$ and building blocks $C_4$ may be modified in that the number of functional groups of building block $C_4$ is reduced from 4 to 2. As $C_2$ contains two functional groups only, $C_2$ may not be regarded as "building block" according to the above definition; its addition to the polymeric backbone does not generate a new branch per se. However, the addition of $C_2$ is required to enable the addition of further building blocks $AB_m$ to the growing polymer finally resulting in an increase of the number of branches. Therefore, the polymerization product also constitutes a hyperbranched polymer. To distinguish compounds not generating further branches per se from building blocks, for the purpose of the present invention compounds such as $C_2$ may be denoted as "monomers". Such a hyperbranched polymer may be written as $(AB_m)_n(C_2)_r$. It is an essential feature of such a system in which a building block is polymerized in the presence of a monomer that the functional groups of the monomer are not capable of reacting with one another. Therefore, every monomer may only be covalently bonded to building blocks and hence, no polymer branches are possible which are exclusively composed of monomers. For the purpose of the present specification the term "hyperbranched polymer" is preferably defined as a polymer composed of at least one type of building block $AB_m$ having complementary functional groups A and B, i.e. functional group A is capable of reacting with functional group B but not with functional group A and functional group B is capable of reacting with functional group A but not with functional group B; or at least one type of building block $AB_m$ having non-complementary functional groups, i.e. functional groups which may not directly react with one another but which may be covalently bonded through at least one type of building block $C_q$ (index $q \geq 3$, preferably 3 or 4) and/or through at least one type of monomer $C_2$ having functional groups C which are complementary to functional groups A and B; i.e. functional group A is capable of reacting with functional group C but neither with functional group A nor B, functional group B is capable of reacting with functional group C but neither with functional group A nor B, and functional group C is capable of reacting with functional groups A and B but not with functional group C.

In addition to the polymeric structure, other biofunctional constituents can be added to the therapeutic composition.

Antibacterial agents such as antibiotics and bactericides, and fungicides are known in the art and are useful herein as a characteristic use agent. Nonlimiting examples of useful antibacterial agents and fungicides include, .beta.-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chloretracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline, hydrochloride, oxytetracycline hydrochloride, clindamycin hydrochloride, ethambutol hydrochloride, metronidazole hydrochloride, pentamidine hydrochloride, gentamicin sulfate, kanamcyin sulfate, lineomycin hydrochloride, methacycline hydrochloride, methenamine hippurate, methenamine mendelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xyleneol, nystatin, tolnaftate and clotrimazole.

Skin lightening agents are known in the art and are useful herein as a characteristic use agent. Nonlimiting examples of useful skin lightening agents include glycosides of hydroxysalicylic acid and/or the glycosides of aliphatic esters of hydroxysalicylic acid as described in U.S. Pat. No. 5,700,784 incorporated by reference herein, hydroquinone, kojic acid or a derivative thereof, especially the salts or esters thereof as described in U.S. Pat. No. 5,279,834 incorporated by reference herein, 3-hydroxy-4(H)-pyran-4-one and its 3-acyl derivatives as described in U.S. Pat. No. 4,545,982 incorporated by reference herein, and 4-hydroxy-5-methyl-3[2H]-furanone.

Artificial tanning agents and accelerators are known in the art and are useful herein as a characteristic use agent. Nonlimiting examples of useful artificial tanning agents and accelerators include dihydroxyacetone, tyrosine, tyrosine esters such as ethyl tyrosinate, and phospho-DOPA.

Anti-Acne Actives are known in the art and are useful herein as a characteristic use agent. Nonlimiting examples of useful anti-acne actives include the keratolytics such as salicylic acid (o-hydroxy-benzoic acid), derivatives of salicylic acid such as 5-octanoyl salicylic acid, and resorcinol; retinoids such as retinoic acid and its derivatives (e.g., cis and trans); sulfur-containing D and L amino acids other than cysteine and their derivatives and salts, particularly their N-acetyl derivatives; lipoic acid; antibiotics and antimicrobials such as benzoyl peroxide, octopirox, tetracycline, 2,4,4'-trichloro-2'-hydroxydiphenyl ether, 3,4,4'-trichlorobanilide, azelaic acid and its derivatives, phenoxyethanol, phenoxypropanol, phenoxisopropanol, ethyl acetate, clindamycin and melclocycline; sebostats such as flavonoids; and bile salts such as scymnol sulfate and its derivatives, deoxycholate, and cholate.

Antiviral agents are also known in the art and useful herein as a characteristic use agent. Nonlimiting examples of antiviral agents include acyclovir, vidarabine, penciclovir, trifluridine, idoxuridine, podophyllotoxin and carbenoxolone.

Free radical scavengers and antioxidants are known in the art and are useful herein as a characteristic use agent. Nonlimiting examples of useful free-radical scavengers and antioxidants include butylated hydroxytoluene (BHT), butylated hydroxyanisole (BHA), tocopherols and their derivatives, ascorbic acid, its salts, derivatives such as ascorbyl palmitate and their salts, retinol and related carotenoids, bioflavonoids such as hesperitin, naringen, rutin, and quercetin, indole-3-carbinol, pycnogenol, melatonin, sulforaphane, pregnenolone, lipoic acid, amide and derivatives, 4-hydroxy-5-methyl-3[2H]-furanone, ferruginol type compounds and esters of cinnamic acid.

The following examples are meant to be illustrative, and not limiting.

Example 1

Synthesis of Base Polymer

A poloxamer triol such as dry (<300 ppm H2O) Multranol 3901 (Bayer, Morristown, N.J.) containing 1 mole of hydroxyl groups is combined with toluene diisocyanate containing 2 moles of NCO groups in a glass reactor equipped with a stirrer, heating jacket and temperature sensor. The reactor is purged with dry nitrogen and the mixture stirred. The reaction volume is heated to 40° C. and allowed to react until the exotherm has subsided. Then the temperature of the reactor is increased in 5° C. increments, stopping after each increment to let the exotherm subside, until a temperature of 65° C. is reached. The reaction mixture is further reacted until 1 mole of isocyanate group is consumed. This end point can be determined by measuring the % NCO.

Example 2

Sunscreen Polymer

The polymer base of Example 1 is placed in a reactor. The reactor is purged with dry nitrogen. The volume is stirred and equivalents of sunblock molecule are delivered to the reaction volume. The ratio of NCO groups in Example 1 and OH groups of the sunblock molecules is chosen to achieve a ratio of sunblock constituents and a ratio between tissue bonding NCO and end-bonded sunblock constituents. The polymer base will immediately begin to react with the introduced constituents. A solvent may be used in cases where the polymer base is too viscous. For example, acetone can be used, and the solvent later removed by vacuum. Alternatively an inert solvent such as propylene carbonate may be used. The reaction is continued for approximately 12 hours at room temperature, in less time at elevated temperature. The reaction is complete when all residual NCO functionality reaches a desired % NCO, which is typically 1-2%.

Embodiments of the invention have described in detail, and other embodiments and modifications will be apparent to those skilled in the art. The following claims are intended to include all such embodiments, modifications and equivalents.

The invention claimed is:

1. A sunscreen skin bonding mixture comprising: (i) a polymerization product of at least one polyol with at least one diisocyanate and at least one UV-A and/or UV-B absorber and ii) a carrier in an amount suitable for application to the skin, wherein at least one terminal isocyanate group persists post-polymerization, and wherein the polymerization product is capable of covalently bonding to the skin tissue of a subject at the terminal isocyanate group.

2. The mixture of claim 1, wherein the polyol is amphiphilic comprising a block structure of ethylene oxide and propylene oxide wherein each block contains 10 to 60 carbon atoms.

3. The mixture of claim 1, wherein the polymerization product of polyol, isocyanate and UV blockers possesses a NCO weight fraction of less than 20% of the total weight.

4. The mixture of claim 1, wherein the polymerization product comprises three arms, one arm with a terminal NCO group, one arm with a terminal UV-A absorber group, and one arm with a terminal UV-B absorber group.

5. The mixture of claim 1, wherein the polyol is a polymerization product of trimethylolpropane, diisocyanate and a poloxamer, characterized in that the end result is a polyol comprising three arms of poloxamer bonded to one trimethylolpropane.

6. A sunblock molecule comprising
a polymer backbone having covalently bonded thereto:
(i) at least one UVA absorber and/or UVB absorber; and
(ii) at least one terminal isocyanate group,
wherein the sunblock molecule is capable of covalently bonding to the skin tissue of a subject at the terminal isocyanate group.

7. The sunblock molecule of claim 6, wherein the at least one UVA absorber and/or UVB absorber is bonded to the polymer backbone by a diisocyanate group.

8. The sunblock molecule of claim 7, wherein the diisocyanate group forms a urethane bond with the polymer backbone.

9. The sunblock molecule of claim 6, wherein the polymer backbone is a polyether.

10. The sunblock molecule of claim 6, wherein the polymer backbone contains a 10-60 carbon block of ethylene oxide and a 10-60 carbon block of propylene oxide.

11. The sunblock molecule of claim 6, wherein the sunblock molecule possesses a NCO weight fraction of less than 20% of the total weight.

12. The sunblock molecule of claim 6, wherein the sunblock molecule has a molecular weight between 1000 and 20,000 Daltons.

13. A sunscreen composition comprising the sunblock molecule of claim 6 and a carrier suitable for application to the skin of a subject.

14. The sunscreen composition of claim 13, wherein three days after applying the sunscreen to the skin of a subject, the SFP of the sunscreen is at least 50% of the SPF of the sunscreen upon application to the skin.

15. The sunscreen composition of claim 13, wherein the carrier (ii) contains free sunblock molecules and a skin emollient.

* * * * *